United States Patent [19]

Röchling et al.

[11] Patent Number: 5,227,402
[45] Date of Patent: Jul. 13, 1993

[54] CONCENTRATED AQUEOUS MICROEMULSIONS

[75] Inventors: Hans Röchling, Bad Soden am Taunus; Konrad Albrecht, Kelkheim, both of Fed. Rep. of Germany

[73] Assignee: Hoechst Aktiengesellschaft, Frankfurt am Main, Fed. Rep. of Germany

[21] Appl. No.: 399,218

[22] Filed: Aug. 28, 1989

Related U.S. Application Data

[62] Division of Ser. No. 76,010, Jul. 21, 1987, Pat. No. 4,870,103.

[30] Foreign Application Priority Data

Jul. 23, 1986 [DE] Fed. Rep. of Germany ....... 3624910

[51] Int. Cl.$^5$ ............................................. A61K 31/275
[52] U.S. Cl. ..................................... 514/521; 514/532
[58] Field of Search ................................ 514/521, 532

[56] References Cited

U.S. PATENT DOCUMENTS 2,819,198  1/1958  Goodhue .............................. 167/42
4,400,196  8/1983  Albrecht et al. ........................ 71/86
4,594,096  6/1986  Albrecht et al. ........................ 71/93

FOREIGN PATENT DOCUMENTS 0160182  6/1985  European Pat. Off. .

OTHER PUBLICATIONS

Wright et al. 104 CA:2187f 1986.

Primary Examiner—Frederick E. Waddell
Assistant Examiner—Russell Travers
Attorney, Agent, or Firm—Curtis, Morris & Safford

[57] ABSTRACT

The invention relates to plant protection agents based on aqueous microemulsions which contain, as emulsifiers, ethoxylated and phosphorylated, styryl-substituted phenols or salts thereof in combination with one or more non-phosphorylated emulsifiers belonging to the group comprising salts of ($C_{10}$–$C_{16}$)-alkyl-monoglycol to -hexaglycol ether-sulfates, salts of $\alpha$-($C_{14}$–$C_{19}$)-alkenol sulfates, salts of optionally chlorinated ($C_{13}$–$C_{18}$)-alkanesulfonic acids, salts of dodecylphenylsulfonic acid, amine oxethylates or $\alpha(C_9$–$C_{20})$-alkyl-$\omega$-hydroxypolyoxyethylenes containing 2 to 22 moles of ethylene oxide.

5 Claims, No Drawings

CONCENTRATED AQUEOUS MICROEMULSIONS

This application is a division of application Ser. No. 076,010, filed Jul. 21, 1987, now U.S. Pat. No. 4,870,103.

The present invention relates to new concentrated aqueous microemulsions for use in plant protection, containing a combination of phosphorylated surfactants with certain non-phosphorylated surfactants. When this combination of surfactants is used, concentrated aqueous emulsions are obtained in the form of transparent microemulsions having advantageous properties in use.

Microemulsions have particle sizes varying essentially between 3 and 10 nm. The preparation form of these aqueous microemulsions can be used for active compounds which hitherto have been formulated as emulsifiable concentrates containing a high proportion of solvent. In contrast with the microemulsions mentioned, these latter concentrates have a higher toxicity for the user. As a result of the lower solvent content, the new microemulsions have a higher flash point. They can therefore be handled with less risks.

The preparation of microemulsions is described in German Offenlegungsschriften 3,009,944 and 3,235,612 and in EP-A 0,107,023 and 0,160,182. However, the processes described in these publications cannot be used for the active compounds mentioned below; in these cases they result in unstable or highly viscous formulations.

It has now been found, surprisingly, that by using a combination of phosphorylated emulsifiers with selected non-phosphorylated emulsifiers, it is possible to process a large number of plant protection active compounds to give transparent, stable microemulsions.

The present invention therefore relates to plant protection agents based on aqueous microemulsions which contain, as emulsifiers, ethoxylated and phosphorylated, styryl-substituted phenols or salts thereof (emulsifier type I), in combination with one or more non-phosphorylated emulsifiers belonging to the group comprising ($C_{10}$–$C_{16}$)-alkylmonoglycol to -hexaglycol ether-sulfate salts, α-($C_{14}$–$C_{19}$)-alkenol sulfates, salts of optionally chlorinated ($C_{13}$–$C_{18}$)-alkanesulfonic acids, salts of dodecylphenylsulfonic acid, amine oxethylates or α-($C_9$–$C_{20}$)-alkyl-ω-hydroxypolyoxethylenes having 2 to 22 moles of ethylene oxide (each belonging to emulsifier type II).

Amongst the emulsifier types II, the compounds containing sulfonic acids or sulfates are preferred.

The phosphorylated and ethoxylated, styryl-substituted phenols (emulsifier type I) can contain 10 to 40 moles of ethylene oxide. These types of compounds are described, for example, in EP-A 163,598.

The phosphorylated surfactants can be employed in the form of acids, but in most cases they are used in the form of salts.

Amongst the salts—and this also applies to the other emulsifier salts—the alkali or alkaline earth metal salts and the ammonium, monoalkylammonium, dialkylammonium or trialkylammonium or the monoalkanolammonium, dialkanolammonium or trialkanolammonium salts should be singled out particularly.

Suitable styryl-containing, ethoxylated and phosphorylated phenols are preferably phenols of this type having three styrene radicals and containing approx. 16 to 20 moles of ethylene oxide. In particular, it is possible to employ oxethylated and phosphorylated tristyrylphenols which have been neutralized with triethanolamine. (®Soprophor FL, made by Rhone Poulenc; and HOE S 3475, made by HOECHST AG). The abovementioned salts of ($C_{13}$–$C_{18}$)-alkanesulfonic acids of emulsifier type II preferably contain secondary alkyl radicals.

The chlorinated compounds contain, in particular, 1.2 to 1.6 moles of Cl per mole of alkanesulfonic acid. Of these, the Na and Ca salts are preferred.

Examples of amine oxethylates which can be employed are coconut fatty amine, stearylamine, oleylamine or tallow fatty amine containing 2 to 25 moles of ethylene oxide.

In addition to the abovementioned combination partners for the ethoxylated and phosphorylated tristyrylphenols, it is also possible to employ, in addition, the following auxiliary emulsifiers:

Ethoxylated castor oils containing 36 to 42 moles of EO; ($C_{16}$–$C_{20}$)-alkanols which have been reacted with 1 to 15 moles of propylene oxide and then with 1 to 30 moles of ethylene oxide; polymerization products formed from propylene oxide and ethylene oxide and containing 10 to 80% by weight of ethylene oxide and 90 to 20% by weight of propylene oxide; n-butanol/-propylene oxide/ethylene oxide block oxalkylates; xylenol oxethylates containing 3 to 5 moles of ethylene oxide, ethoxylated ($C_8$–$C_{12}$)-alkylphenols or propoxylated and ethoxylated tributylphenols.

The ethoxylated alkylphenols mentioned preferably contain 8 to 12 moles of ethylene oxide. Propoxylated and ethoxylated tributylphenols are to be understood as meaning, in particular, those which are obtained by reacting tributylphenols with 8 to 12 moles of propylene oxide and then with 1 to 30 moles of ethylene oxide.

Combination partners for emulsifier type I which should be mentioned particularly preferably are the sodium salts of alkyl-monoglycol to -hexaglycol ethersulfates in which the alkyl radicals are composed to the extent of 75–70% of $C_{12}$-alkyl and to the extent of 25 to 30% of $C_{14}$-alkyl (commercial product (®)genapol LRO, HOECHST AG).

The quantitative proportion in the emulsifier combination of phosphorylated and non-phosphorylated emulsifiers can be 2.0 to 40% by weight, especially 8.0 to 25% by weight, relative to the total formulation. 0.5 to 35% by weight, but especially 2.0 to 18% by weight, of oxethylated and phosphorylated polystyrylphenol (type I) can be present. Non-phosphorylated emulsifier (type II) can be present to the extent of 0.1 to 25% by weight, in particular 0.5 to 10% by weight, in the formulations according to the invention. The water content varies between 10 and 60% by weight.

The active compound content in the microemulsions according to the invention is between 0.5 and 70% by weight, in particular between 10 and 50% by weight.

In addition to the combination of phosphorylated and nonphosphorylated surfactants to be employed in accordance with the invention, the microemulsions can also contain the following additives: antifreeze agents, such as, for example, monohydric or polyhydric alcohols, glycol ethers or urea, especially glycerol, isopropanol, propylene glycol monomethyl ether, dipropylene or tripropylene glycol monomethyl ether or cyclohexanol. The proportion of these antifreeze agents is between 0.5 and 30% by weight.

In order to stabilize or obtain a pH value favorable for the formulation, acids, preferably carboxylic acids, such as, for example, acetic acid or propionic acid, are added in some cases in proportions of 0.5 to 5.0%.

Before the emulsifiers are added, the active compounds are dissolved in small amounts of a solvent. The following can be used in this regard: aromatic solvents, such as, for example, alkylated benzenes and naphthalenes, ketones, such as, for example, isophorone or cyclohexanone, alcohols, such as, for example, ethylhexanol, cyclohexanol or isononanol, and esters, such as, for example, n-butyl acetate, butylglycol acetate or oxo-alkyl acetates in which alkyl represents $(C_6-C_{13})$-alkyl or tridecyl, and also alkyl phthalates. Depending on the active compound to be employed, the formulations can contain up to 40% by weight of solvent.

The microemulsions are prepared by dissolving the active compound in the appropriate solvent or solvent mixture. A solution of the emulsifiers in water is added to this solution with vigorous stirring.

It is also possible to dissolve the emulsifiers together with the active compound in the solvent and to add the water with vigorous stirring, or, in the converse sequence, to stir the active compound or the solution of active compound into the aqueous solution of the emulsifiers.

Active compounds which can be employed for the microemulsions according to the invention are insecticides, nematicides, fungicides, herbicides and combinations of these active compounds with one another; the following are particularly suitable: triazophos, deltamethrin, binapacryl, endosulfan, abamectin, O-ethyl S-(N-phenyl-N-methylcarbamoylmethyl) isopropylamidothiophosphate (HOE 36,275), pyrazophos, diclofopmethyl and fenoxapropethyl. With the exception of HOE 36,275, these active compounds are described in CH. R. Worthing, S. B. Walker, The Pesticide Manual, 7th edition (1983), British Crop Protection Council. HOE 36,275 is disclosed in German Patent No. 2,633,159. Insofar as the compounds can exist as stereoisomers, it is possible to employ the mixtures of isomers or the pure isomers.

Before the microemulsions according to the invention are used, they are diluted with water in order to prepare a spray liquor in the same manner as conventional emulsifiable concentrates.

The following examples serve to illustrate the invention.

EXAMPLE 1

16.5% by weight of tristyrylphenol, oxethylated with 20 moles of EO, phosphorylated, and neutralized with triethanolamine[1b], are dissolved, together with 2.5% by weight of the sodium salt of an alkyldiglycol ether-sulfate[2a], in 61.07% by weight of distilled water by stirring. 19.93% by weight of O-ethyl S-(N-phenyl-N-methylcarbamoylmethyl) isopropylamidothiophosphate are added to this solution, also with stirring. The mixture is stirred for about 12 hours at 25° C. until a transparent, homogeneous emulsion has been formed. A sample is stored at 50° C. for 3 months. The concentrated aqueous emulsion is stable chemically and for application purposes.

EXAMPLE 2

15.5% by weight of tristyrylphenol, oxethylated with 18 moles of EO, phosphorylated and neutralized with triethanolamine[1a] are dissolved, together with 2.7% by weight of the sodium salt of an alkyldiglycol ether-sulfate[2a], 4.5% by weight of an amine oxethylate formed from tallow fatty amine and 20 moles of ethylene oxide, and 6.3% by weight of propylene glycol monomethyl ether, in 51.9% by weight of ®Hostathion (concentrate). 19.1% by weight of distilled water are then added with vigorous stirring. Stirring is continued until a transparent, homogeneous emulsion has been formed. A sample is stored for 14 days at 54° C. and for 3 months at 40° C. The formulation is stable chemically and for application purposes.

EXAMPLE 3

2.54% by weight of 96% strength deltamethrin are dissolved in 23.5% by weight of cyclohexanone. A solution of 2.90% by weight of the sodium salt of an alkyldiglycol ether-sulfate[2a], 14.60% by weight of tristyrylphenol, oxethylated with 20 moles of EO, phosphorylated, and neutralized with triethanolamine[1b], and 0.98% by weight of acetic acid in 55.48% by weight of distilled water is added to the solution with vigorous stirring. The mixture is stirred until a homogeneous microemulsion has been formed. A sample is stored at 50° C. for 3 months. The formulation is stable chemically and for application purposes.

EXAMPLE 4

29.0% by weight of 97.8% strength binapacryl are dissolved in a mixture of 25.0% by weight of cyclohexanone and 10.0% by weight of cyclohexanol. A solution of 15.0% by weight of tristyrylphenol, oxethylated with 20 moles of EO, phosphorylated, and neutralized with triethanolamine[1b], and 3.0% by weight of the sodium salt of an alkyldiglycol ether-sulfate[2a] in 18.0% by weight of distilled water is added to the solution with vigorous stirring. The mixture is stirred until a homogenous and transparent, concentrated aqueous emulsion is obtained. The formulation is stable chemically and for application purposes after being stored at 50° C. for 3 months.

EXAMPLE 5

5.4% by weight of calcium dodecylbenzenesulfonate (70% strength) in isobutanol and 4.1% by weight of castor oil, reacted with 36 moles of EO, and 6.7% by weight of tristyrylphenol, oxethylated with 20 moles of EO, phosphorylated, and neutralized with triethanolamine[1b], are dissolved in 20.8% by weight of water, and a solution of 31.8% by weight of endosulfan in a mixture of 15.1% by weight of ®Solvesso 200 and 16.1% by weight of cyclohexanon is added with vigorous stirring. The mixture is stirred until a homogeneous microemulsion has been formed. The formulation is stable chemically and for application purposes after being stored at 54° C. for 14 days.

EXAMPLE 6

21.1% by weight of 95.1% strength endosulfan and 10.3% by weight of 97.8% strength binapacryl are dissolved in a mixture of 20.0% by weight of cyclohexanone and 10.0% by weight of cyclohexanol. A solution of 15.0% by weight of tristyrylphenol, oxethylated with 20 moles of EO, phosphorylated, and neutralized with triethanolamine[1b], and 3.0% by weight of the sodium salt of an alkyldiglycol ether-sulfate[2a] in 20.6% by weight of distilled water is added to the solution with vigorous stirring.

A homogeneous, transparent emulsion is formed. A sample is stored at 50° C. for 3 months. The formulation is stable chemically and for application purposes.

EXAMPLE 7

45.5% by weight of a 60% strength solution of pyrazophos in ®Solvesso 200 are mixed with 22.7% by weight of cyclohexanol. A solution of 10.9% by weight of tristyrylphenol, oxethylated with 20 moles of EO, phosphorylated, and neutralized with triethanolamine[1b], and 2.7% by weight of the sodium salt of an alkyldiglycol ether-sulfate[2a] in 18.2% by weight of water is added to this mixture with vigorous stirring. The mixture is stirred until a homogeneous, transparent emulsion has been formed. The formulation is stable chemically and for application purposes after being stored at 50° C. for 3 months.

EXAMPLE 8

45.5% by weight of a 60% strength solution of pyrazophos in Solvesso 200 are mixed with 8.2% by weight of cyclohexanol. A solution of 5.4% by weight of tristyrylphenol, oxethylated with 20 moles of EO, phosphorylated, and neutralized with triethanolamine[1b], 0.2% by weight of the sodium salt of an alkyldiglycol ether-sulfate[2a] and 22.5% by weight of nonylphenol, ethoxylated with 10 EO, in 18.2% by weight of water is added to this mixture with vigorous stirring. A homogeneous microemulsion is formed, which is stable chemically and for application purposes after being stored for 14 days.

EXAMPLE 9

45.5% by weight of a 60% strength solution of pyrazophos in ®Solvesso 200 are mixed with 8.2% by weight of cyclohexanol. A solution of 5.4% by weight of tristyrylphenol, oxethylated with 20 moles of EO, phosphorylated, and neutralized with triethanolamine[1b], 0.2% by weight of the sodium salt of an alkyldiglycol ether-sulfate[2a] and 22.5% by weight of tributylphenol, ethoxylated with 11 moles of EO, in 18.2% by weight of water is added to this mixture with vigorous stirring. A homogeneous, transparent emulsion is formed, which is stable chemically and for application purposes after being stored at 54° C. for 14 days.

EXAMPLE 10

45.5% by weight of a 60% strength solution of pyrazophos in ®Solvesso 200 are mixed with 5.4% by weight of cyclohexanol. A solution of 8.2% by weight of tristyrylphenol, oxethylated with 20 moles of EO, phosphorylated, and neutralized with triethanolamine[1b] and 22.7% by weight of an α-alkyl-omega-hydroxypolyoxyethylene[2b] containing 8 EO units, alkyl representing $C_{13}$, in 18.2% by weight of water is added to this mixture with vigorous stirring. The mixture is stirred until a homogeneous microemulsion has been formed. A sample is stored at 54° C. for 14 days. The formulation is stable chemically and for application purposes.

EXAMPLE 11

2.0% by weight of abamectin are dissolved in 22.0% by weight of cyclohexanone, and a solution of 15.0% by weight of tristyrylphenol, oxethylated with 20 moles of EO, phosphorylated, and neutralized with triethanolamine[1b], and 3.0% by weight of the sodium salt of an alkyldiglycol ether-sulfate[2a] in 58.0% by weight of distilled water is added with vigorous stirring. This gives a homogeneous, transparent emulsion which is stable for application purposes and chemically after being stored at 54° C. for 14 days.

EXAMPLE 12

24.0% by weight of diclofopmethyl are dissolved in 19.0% by weight of cyclohexanone and added, with vigorous stirring, to a solution of 3.0% by weight of the sodium salt of an alkyldiglycol ether-sulfate[2a], 17.0% by weight of tristyrylphenol, oxethylated with 20 moles of EO, phosphorylated, and neutralized with triethanolamine[1b], and 17.0% by weight of propyleneglycol monomethyl ether in 20.0% by weight of water. The mixture is stirred until a transparent, homogeneous emulsion has been formed. The formulation is stable for application purposes and chemically at 54° C. and at 0° C.

EXAMPLE 13

8.0% by weight of fenoxapropethyl are dissolved in 10.0% by weight of Solvesso 200, 15.0% by weight of cyclohexanone and 4.0% by weight of diethyl phthalate, and the solution is added with vigorous stirring to a solution of 18.0% by weight of tristyrylphenol, oxethylated with 20 moles of EO, phosphorylated, and neutralized with triethanolamine[1b], 3.0% by weight of the sodium salt of an alkyldiglycol ether-sulfate[2a] and 22.0% by weight of propyleneglycol monomethyl ether in 20.0% by weight of water. The mixture is stirred until a transparent emulsion has been formed. The formulation is stable for application purposes and chemically at 54° C. and at 0° C.

EXAMPLE 14

16.5% by weight of tristyrylphenol, oxethylated with 20 moles of EO, phosphorylated, and neutralized with potassium hydroxide are dissolved, together with 2.5% by weight of the sodium salt of an alkyldiglycol ether-sulfate[2a], in 61.07% by weight of distilled water, with stirring. 19.93% by weight of O-ethyl S-(N-phenyl-N-methylcarbamoylmethyl) isopropylamidothiophosphate are added to this solution, also with stirring. The mixture is stirred for about 12 hours at 25° C., until a transparent, homogeneous emulsion has been formed. A sample is stored at 50° C. for 3 months. The concentrated aqueous emulsion is stable chemically and for application purposes.

EXAMPLE 15

15.5% by weight of tristyrylphenol, oxethylated with 18 moles of EO, phosphorylated, and neutralized with potassium hydroxide, are dissolved, together with 2.7% by weight of the sodium salt of an alkyldiglycol ether-sulfate[2a], 4.5% by weight of an amine oxethylate formed from tallow fatty amine and 20 moles of ethylene oxide, and 6.3% by weight of propylene glycol monomethyl ether, in 51.9% by weight of (®) Hostathion (Concentrate). 19.1% by weight of distilled water are then added with vigorous stirring. Stirring is continued until a transparent, homogeneous emulsion has been formed. A sample is stored for 14 days at 54° C. and for 3 months at 40° C. The formulation is stable chemically and for application purposes.

EXAMPLE 16

2.54% by weight of 96% deltamethrin are dissolved in 23.5% by weight of cyclohexanone. A solution of 2.90% by weight of the sodium salt of an alkyldiglycol ethersulfate[2a], 14.60% by weight of tristyrylphenol, oxethylated with 20 moles of EO, phosphorylated, and neutralized with potassium hydroxide, and 0.98% by weight of acetic acid in 55.48% by weight of distilled water is added to the solution with vigorous stirring. The mixture is stirred until a homogeneous microemulsion has been formed. A sample is stored at 50° C. for 3 months. The formulation is stable chemically and for application purposes.

EXAMPLE 17

29.0% by weight of 97,8% binapacryl are dissolved in a mixture of 25.0% by weight of cyclohexanone and 10.0% by weight of cyclohexanol. A solution of 15.0% by weight of tristyrylphenol, oxethylated with 20 moles of EO, phosphorylated, and neutralized with sodium hydroxide, and 3.0% by weight of the sodium salt of an alkyldiglycol ether-sulfate[2a] in 18.0% by weight of distilled water is added to the solution with vigorous stirring. The mixture is stirred until a homogeneous and transparent, concentrated aqueous emulsion is obtained. The formulation is stable chemically and for application purposes after being stored at 50° C. for 3 months.

EXAMPLE 18

5.4% by weight of calcium dodecyl benzene sulfonate (70%) in isobutanol and 4.1% by weight of castor oil, reacted with 36 moles of EO, and 6.7% by weight of tristyrylphenol, oxethylated with 20 moles of EO, phosphorylated, and neutralized with potassium hydroxide, are dissolved in 20.8% by weight of water, and a solution of 31.8% by weight of endosulfan in a mixture of 15.1% by weight of ®Solvesso 200 and 16.1% by weight of cyclohexanone is added, with vigorous stirring. The mixture is stirred until a homogeneous microemulsion has been formed. The formulation is stable chemically and for application purposes after being stored at 54° C. for 14 days.

EXAMPLE 19

21.1% by weight of 95.1% endosulfan and 10.3% by weight of 97.8% binapacryl are dissolved in a mixture of 20.0% by weight of cyclohexanone and 10.0% by weight of cyclohexanol. A solution of 15.0% by weight of tristyrylphenol, oxethylated with 20 moles EO, phosphorylated, and neutralized with sodium hydroxide, and 3.0% by weight of the sodium salt of an alkyldiglycol ether-sulfate[2a] in 20.6% by weight of distilled water is added to the solution with vigorous stirring.

A homogeneous, transparent emulsion is formed. A sample is stored at 50° C. for 3 months. The formulation is stable chemically and for application purposes.

EXAMPLE 20

45.5% by weight of a 60% strength solution of pyrazophos in ®Solvesso 200 are mixed with 22.7% by weight of cyclohexanol. A solution of 10.9% by weight of tristyrylphenol, oxethylated with 20 moles of EO, phosphorylated, and neutralized with potassium hydroxide, and 2.7% by weight of the sodium salt of an alkyldiglycol ether-sulfate[2a] in 18.2% by weight of water is added to this mixture with vigorous stirring. The mixture is stirred until a homogeneous, transparent emulsion has been formed. The formulation is stable chemically and for application purposes after being stored at 50° C. for 3 months.

EXAMPLE 21

45.5% by weight of a 60% strength solution of pyrazophos in Solvesso 200 are mixed with 8.2% by weight of cyclohexanol. A solution of 5.4% by weight of tristyrylphenol, oxethylated with 20 moles of EO, phosphorylated, and neutralized with sodium hydroxide, 0.2% by weight of the sodium salt of an alkyldiglycol ether-sulfate[2a] and 22.5% by weight of nonylphenol, ethoxylated with 10 EO, in 18.2% by weight of water is added to this mixture with vigorous stirring. A homogeneous microemulsion is formed, which is stable chemically and for application purposes after being stored for 14 days.

EXAMPLE 22

45.5% by weight of a 60% strength solution of pyrazophos in (®)Solvesso 200 are mixed with 8.2% by weight of cyclohexanol. A solution of 5.4% by weight of tristyrylphenol, oxethylated with 20 moles of EO, phosphorylated, and neutralized with potassium hydroxide, 0.2% by weight of the sodium salt of an alkyldiglycol ether-sulfate[2a] and 22.5% by weight of tributylphenol, ethoxylated with 11 moles of EO, in 18.2% by weight of water is added to this mixture with vigorous stirring. A homogeneous, transparent emulsion is formed, which is stable chemically and for application purposes after being stored at 54° C. for 14 days.

EXAMPLE 23

45.5% by weight of a 60% strength solution of pyrazophos in (®)Solvesso 200 are mixed with 5.4% by weight of cyclohexanol. A solution of 8.2% by weight of tristyrylphenol, oxethylated with 20 moles of EO, phosphorylated, and neutralized with potassium hydroxide, and 22.7% by weight of α-alkyl-omega-hydroxypolyoxyethylene[2b] containing 8 units of EO, alkyl representing $C_{13}$, in 18.2% by weight of water is added to this mixture with vigorous stirring. The mixture is stirred until a homogeneous microemulsion has been formed. A sample is stored at 54° C. for 14 days. The formulation is stable chemically and for application purposes.

EXAMPLE 24

2.0% by weight of abamectin are dissolved in 22.0% by weight of cyclohexanon, and a solution of 15.0% by weight of tristyrylphenol, oxethylated with 20 moles of EO, phosphorylated, and neutralized with potassium hydroxide, and 3.0% by weight of the sodium salt of an alkyldiglycol ether-sulfate[2a] in 58.0% by weight of distilled water is added, with vigorous stirring. This gives a homogeneous, transparent emulsion which is stable for application purposes and chemically after being stored at 54° C. for 14 days.

EXAMPLE 25

24.0% by weight of diclofopmethyl are dissolved in 19.0% by weight of cyclohexanone and are added, with vigorous stirring, to a solution of 3.0% by weight of the sodium salt of an alkyldiglycol ether-sulfate[2a], 17.0% by weight of tristyrylphenol, oxethylated with 20 moles of EO, phosphorylated, and neutralized with potassium hydroxide, and 17.0% by weight of propyleneglycol monomethyl ether in 20.0% by weight of water. The mixture is stirred until a transparent, homogeneous emulsion has been formed. The formulation is stable for

EXAMPLE 26

8.0% by weight of fenoxapropethyl are dissolved in 10.0% by weight of Solvesso 200, 15.0% by weight of cyclohexanone and 4.0% by weight of diethyl phthalate, and are added, with vigorous stirring, to a solution of 18.0% by weight of tristyrylphenol, oxethylated with 20 moles of EO, phosphorylated, and neutralized with sodium hydroxide, 3.0% by weight of the sodium salt of an alkyldiglycol ether-sulfate[2a] and 22.0% by weight of propylene glycol monomethyl ether in 20.0% by weight of water. The mixture is stirred until a transparent emulsion has been formed. The formulation is stable for application purposes and chemically at 54° C. and at 0° C.

1a) and 1b): Emulsifier type I (1a: (®)Soprophor FL; 1b: HOE 3475
2a) and 2b): Emulsifier type II (2a: (®)Genapol LRO; 2b): (®)Genapol-X-080, both made by HOECHST AG)

We claim:

1. A plant protection composition based on an aqueous microemulsion of high storage stability wherein the active compound employed is the compound abamectin and which contains, as emulsifiers, 0.5 to 35% by weight of ethoxylated and phosphorylated, styryl-substituted phenols or salts thereof containing 1 to 4 styryl-radicals and 10 to 40 moles of ethylene oxide in combination with 0.1 to 25% by weight of non-phosphorylated emulsifiers belonging to the group comprising salts of ($C_{10}$–$C_{16}$)-alkyl-monoglycol to -hexaglycol ether-sulfates.

2. A plant protection composition as in claim 1, which contains 2 to 40% by weight of emulsifiers, 10–60% by weight of water and 0.5 to 70% by weight of the active compound abamectin.

3. A plant protection composition as in claim 1, which contains 2 to 18% by weight of phosphorylated emulsifiers.

4. A plant protection composition as in claim 1, which contains 0.5 to 10% by weight of non-phosphorylated emulsifiers.

5. A plant protection composition as in claim 1, which contains 10 to 50% by weight of the active compound abamectin.

* * * * *